United States Patent [19]

Page et al.

[11] Patent Number: 4,913,892

[45] Date of Patent: Apr. 3, 1990

[54] PREPARATION AND USE OF NEW SOLVATES OF BECLOMETHASONE 17,21-DIPROPIONATE

[75] Inventors: Philip R. Page, Parede; William Heggie, Barreiro, both of Portugal

[73] Assignee: Hovione Inter Ltd., Switzerland

[21] Appl. No.: 758,287

[22] Filed: Jul. 24, 1985

[30] Foreign Application Priority Data

Jul. 25, 1984 [PT] Portugal ................................ 78972
Jul. 11, 1985 [PT] Portugal ................................ 80796

[51] Int. Cl.$^4$ ..................... A61K 31/56; C07J 1/00; A61L 9/04
[52] U.S. Cl. ..................................... 424/45; 552/574; 514/80
[58] Field of Search ................... 260/397.45; 514/180; 424/45

[56] References Cited

U.S. PATENT DOCUMENTS 4,044,126  8/1977  Cook et al. ......................... 514/180

OTHER PUBLICATIONS

Chemical Abstracts. vol. 80 (1974), Par. 19542(b) relied on.

*Primary Examiner*—Joseph A. Lipovsky
*Attorney, Agent, or Firm*—Ostrolenk, Faber, Gerb & Soffen

[57] ABSTRACT

Preparation of novel solvates of beclomethasone 17,21-dipropionate, by dissolution of beclomethasone 17,21-dipropionate in an ethereal or halogenated hydrocarbon solvent and precipitation by the addition of di-isopropyl ether. These new solvates are bulk stable, in both the micronized and non-micronized forms. The micronized form is especially suitable for the preparation of stable aerosol.

11 Claims, No Drawings

PREPARATION AND USE OF NEW SOLVATES OF BECLOMETHASONE 17,21-DIPROPIONATE

The present invention refers to the preparation of di-isopropyl ether solvates of beclomethasone 17,21-dipropionate. These new solvates are substantially bulk-stable, in both the non-micronised and the micronised forms. The micronised form is especially indicated for use in the preparation of stable aerosol formulations.

The use of beclomethasone 17,21-dipropionate per se in the treatment of asthmatic complaints has been known for some time, for example see Morrow Brown et al., British Medical Journal 1, 585–90 (1972). Since this time, the preparation of stable aerosols has been of significant importance. The use of halogenated hydrocarbons was first described in British Patent 1,429,184, and later in British Patent Application 2,076,422. However, the halogenated hydrocarbon solvates therein produced, including that of beclomethasone 17,21-dipropionate, were found not to be bulk stable. Since that time, other solvates have been claimed, such as hydrocarbon solvates in European Patent Specification 39,369, the ethyl acetate solvate in German Offenlegungschrift 3,018,550 and the monohydrate in British Patent Application 2,107,715.

It is taught in British Patent 1,429,184 that the suitable particle size of a steroid for inhalation into the bronchial system is between 2 and 5 microns. It is further taught that beclomethasone 17,21-dipropionate crystals in aerosol formulations are prone to the phenomenon of crystal growth and/or crystal agglomeration, wherein crystals of particle size above 20 microns are formed. Such crystals can cause clogging of the metering valve in the aerosol, and are also too large to penetrate far enough into the bronchial system.

According to the present invention, there is provided a process for the preparation of new di-isopropyl ether solvates of beclomethasone 17,21-dipropionate, characterised by the fact that beclomethasone 17,21-dipropionate is dissolved in an organic solvent and is precipitated by addition of di-isopropyl ether. A further feature of the present invention are the novel solvates produced by the above process.

We have now found that solvates of beclomethasone 17,21-dipropionate with di-isopropyl ether can be prepared, which are substantially bulk stable with respect to the solvate present. Further, these new solvates can be micronised by conventional methods, such as by a fluid energy mill, and it has been surprisingly found that those micronised solvates are also substantially stable. Further, it has been unexpectedly established that such micronised solvates, when used in aerosol formulations, do not exhibit any significant crystal growth or agglomeration.

The process of the present invention is conveniently carried out using a mixed solvent system, consisting of di-isopropyl ether and an organic solvent, which is both miscible with or soluble in di-isopropyl ether and in which the beclomethasone 17,21-dipropionate is soluble. The preferred organic solvent can be chosen from the group comprising halogenated hydrocarbons such as chloroform and dichloromethane and ethers such as tetrahydrofuran and dioxan.

The beclomethasone 17,21-dipropionate is dissolved in the organic solvent, at between room temperature and the reflux temperature of the organic solvent. Then sufficient di-isopropyl ether is added, with constant stirring, until complete crystallisation occurs. Alternatively, only sufficient organic solvent is used to just dissolve the beclomethasone 17,21-dipropionate, and then di-isopropyl ether is added until the mixture becomes slightly turbid. Upon cooling slowly to about 0° C., the solvate crystallises out of the mixture.

The required crystalline solid can be obtained by conventional means, such as filtration, washing with di-isopropyl ether, followed by drying. The dried solid is then micronised by known techniques, such as by a fluid energy mill or by ball milling. The particle size range is preferably between 2 and 5 microns, which can be obtained either directly from the micronisation technique or by seiving.

The solvates thus obtained have been analysed by various techniques. Thus, the infra-red spectra of beclomethasone 17,21-dipropionate and of a di-isopropyl ether solvate show a significant difference in the region of 3200–3500 cm$^{-1}$. This is due to the fact that in the solvated crystal, hydrogen bonding is eliminated because of the presence of the solvating molecules and this causes the broad band at 3280 cm$^{-1}$ in the non-solvated crystal to move 3500 cm$^{-1}$ in the solvated crystal. Similarly, other differences are apparent, for example in the carbonyl stretching frequencies at approximately 1720 cm$^{-1}$, and in other regions throughout the entire spectra.

In order to ascertain the exact quantity of solvate present, a loss on drying test at 105° C. under vacuum can be conveniently used. It has been thus shown that the loss on drying is usually about 10% weight/weight.

An analysis by gas chromatography indicated that both the di-isopropyl ether, and the organic solvent used in the crystallisation mixture, were incorporated into the crystal structure of the solvate.

A further feature of the invention is a stable aerosol formulation containing the solvates prepared as above. The propellants and actual aerosol cannisters and valves to be used are well known to those skilled in the art. Preferably, the propellants comprise trichlorofluoromethane (Freon 11 ®) and dichlorodifluoromethane (Freon 12 ®).

Typically the aerosol will supply metered doses of 50 μg of the active principle. The usual maximum daily dose is about 600 μg of beclomethasone 17,21-dipropionate. The presence of about 10% weight/weight of di-isopropyl ether plus the organic solvent used in the crystallisation mixture is thus not considered to have any significant toxic effect.

The following examples will serve to illustrate the invention, without in any way limiting the scope thereof.

EXAMPLE 1

Preparation of Beclomethasone 17,21-dipropionate di-isopropyl ether solvate

Method A:

Beclomethasone 17,21-dipropionate (100.0 g; 0.192 moles) was dissolved in chloroform (1 lt.). The solution was filtered and di-isopropyl ether (4 lts.) was added with constant stirring. The stirring was then continued for a further hour, the solid so formed was then filtered, washed with a small quantity of di-isopropyl ether and dried at 35° C. The yield of the solvate was 104.9 g.

The product had the following analysis:

| Loss on drying | 10.8% | (dried under vacuum at 105° C. to constant weight) |
|---|---|---|
| Gas chromatography | 6.9% | (di-isopropyl ether) |
| | 3.0% | (chloroform) |
| Karl Fischer | 0.4% | (water) |
| Melting point | 210–2° C. | |

Method B:

Beclomethasone 17,21-dipropionate (50.0 g; 0.096 moles) was dissolved in chloroform (500 ml) and the resulting solution filtered. Di-isopropyl ether saturated with water (2 lts.) was then added with constant stirring and the stirring then continued for a further hour. The precipitate was filtered, washed with di-isopropyl ether and dried at 35° C. The yield of beclomethasone 17,21-dipropionate di-isopropyl ether solvate was 47.7 g and had the following analysis:

| Loss on drying | 12.7% | (dried under vacuum at 105° C constant weight) |
|---|---|---|
| Gas chromatography | 6.9% | (di-isopropyl ether) |
| | 4.5% | (chloroform) |
| Karl Fischer | 0.57% | (water) |
| Melting point | 21–2° C. | |

Method C:

Dioxan (500 ml) was added to beclomethasone 17,21-dipropionate (100.0 g; 0.192 moles) and the mixture warmed to dissolve the solid material. The solution was then filtered and di-isopropyl ether (5 lts.) added with constant stirring. After complete precipitation, the mixture was cooled in an ice bath and the solid filtered, then washed with di-isopropyl ether and dried at 35° C. The yield of the dioxan/di-isopropyl ether solvate was 110.5 g. After micronisation, the product had the following analysis:

| Loss on drying | 11.4% | (dried under vacuum at 105° C. to constant weight) |
|---|---|---|
| Gas chromatography | 3.0% | (di-isopropyl ether) |
| | 7.2% | (dioxan) |
| Karl Fischer | 0.91% | (water) |
| Melting point | 21–1° C. | |

Method D:

Beclomethasone 17,21-dipropionate (100.0 g; 0.192 moles) was dissolved in tetrahydrofran (500 ml) with slight warming and the resulting solution filtered. Di-isopropyl ether (5 lts.) was then added under constant stirring and the mixture cooled to 0° C. The solid was then filtered, washed with a small quantity of di-isopropyl ether and dried at 35° C. The yield of solvate was 109.1 g. After micronisation, the beclomethasone 17,21-dipropionate tetrahydrofuran/di-isopropyl ether solvate had the following analytical values:

| Loss on drying | 10.5% | (dried under vacuum at 105° C. to constant weight) |
|---|---|---|
| Gas chromatography | 6.5% | (di-isopropyl ether) |
| | 4.5% | (tetrahydrofuran) |
| Karl Fischer | 0.97% | (water) |
| Melting point | 210–1° C. | |

EXAMPLE 2

Oral inhalation spray formulation

A spray formulation of di-isopropyl ether solvate of beclomethasone 17,21-dipropionate can be prepared as follows:

| Beclomethasone 17,21-dipropionate di-isopropyl ether solvate | 10.0 mg |
|---|---|
| Linoleic acid | 10.0 mg |
| Trichlorofluoromethane | 9.99 g |
| Dichlorodifluoromethane | 15.00 g |

The linoleic acid is efficiently mixed with cold trichlorofluoromethane, then the micronised beclomethasone 17,21-dipropionate di-isopropyl ether solvate is added. The mixing is continued until a completely uniform mixture is obtained, with any trichlorofluoromethane lost be evaporation, being replaced. Each inhaler is filled with the required amount after which the valve is attached, and the required dichlorodifluoromethane pumped in.

We claim:

1. Process for the preparation of di-isopropyl ether solvates of beclomethasone 17,21-dipropionate, characterised by the act that beclomethasone 17,21-dipropionate is dissolved in an organic solvent and is precipitated by addition of di-isopropyl ether.

2. Process according to claim 1, characterised by the fact that the organic solvent is chosen from a group consisting of halogenated hydrocarbons and ethers.

3. Process according to claim 2, characterised by the fact that the organic solvent is chloroform or dichloromethane.

4. Process according to claim 2, characterised by the fact that the organic solvent is tetrahydrofuran or dioxan.

5. Process according to claim 1, characterised by the fact that the solvate prepared by this process contains about 10% of solvating substances.

6. Solvates of beclomethasone 17,21-dipropionate produced by the process of claim 1.

7. Solvates according to claim 6, in which the di-isopropyl ether is between 3 and 10% by weight.

8. Solvates according to claim 6 in micronized form.

9. Solvates according to claim 6 in which the organic solvent is tetrahydrofuran.

10. In the preparation of an aerosol in which beclomethasone 17,21-dipropionate and propellant gas are introduced into an aerosol container, the improvement which comprises employing the beclomethasone 17,21-dipropionate as a di-isopropyl ether solvate of beclomethasone 17,21-dipropionate.

11. The preparation according to claim 10 in which the propellant gas comprises a mixture of trichlorofluoromethane and dichlorodifluoromethane.

* * * * *